United States Patent

Prasad et al.

Patent Number: 5,466,852
Date of Patent: Nov. 14, 1995

[54] PROCESS FOR THE PRODUCTION OF S,S,S-TRIBUTYLPHOSPHOROTRITHIOATE

[75] Inventors: Vidyanatha A. Prasad; Peter E. Newallis, both of Leawood, Kans.

[73] Assignee: Bayer Corporation, Pittsburgh, Pa.

[21] Appl. No.: 298,501

[22] Filed: Aug. 30, 1994

Related U.S. Application Data

[63] Continuation of Ser. No. 89,157, Jul. 8, 1993, abandoned.

[51] Int. Cl.$^6$ .................................................... C07F 9/11
[52] U.S. Cl. .................................... 558/122; 558/208
[58] Field of Search ................................ 558/122

[56] References Cited

U.S. PATENT DOCUMENTS

| | | | |
|---|---|---|---|
| 2,059,084 | 10/1936 | Buchhelm | 558/122 |
| 2,682,554 | 6/1954 | Crouch et al. | 260/461 |
| 2,943,107 | 6/1960 | Rattenbury et al. | 260/461 |
| 3,885,002 | 5/1975 | Barber | 260/972 |
| 5,183,916 | 2/1993 | Zakaryan et al. | 558/95 |
| 5,189,195 | 2/1993 | Newallis et al. | 558/208 |

OTHER PUBLICATIONS

S. M. Mehta and M. V. Vakilwala, J. Am. Chem. Soc., 74, 563 (1952).
L. Huestis, J. Chem. Ed., 54, 327 (1977).
D. S. Matteson & R. J. Moody, J. Org. Chem., 45, 1091 (1980).

*Primary Examiner*—Johann Richter
*Assistant Examiner*—Michael G. Ambrose
*Attorney, Agent, or Firm*—Joseph C. Gil; Lyndanne M. Whalen; Godfried R. Akorli

[57] ABSTRACT

S,S,S-tributylphosphorotrithioite is oxidized with a perborate or percarbonate at a pH of from about 6 to about 12 and at a temperature of from about 40° to about 65° C. Sodium perborate is a particularly preferred oxidizing agent. The product S,S,S-tributylphosphorotrithioate may be recovered by simple phase separation.

8 Claims, No Drawings

PROCESS FOR THE PRODUCTION OF S,S,S-TRIBUTYLPHOSPHOROTRITHIOATE

This application is a continuation of application Ser. No. 08/089,157 filed Jul. 8, 1993, now abandoned.

BACKGROUND OF THE INVENTION

The present invention relates to an oxidation process for the production of S,S,S-tributylphosphorotrithioate.

S,S,S-tributylphosphorotrithioate is known to be useful as a defoliant. This defoliant is typically produced by reacting phosphorus trichloride with butyl mercaptan to form S,S,S-tributylphosphorotrithioite (phosphite). The phosphite is then oxidized to form the corresponding S,S,S-tributylphosphorotrithioate.

Processes for the production of phosphite are disclosed, for example, in U.S. Pat. Nos. 2,682,554; 2,943,107; 3,885,002 and 5,183,916.

Processes for the oxidation of phosphite to form the corresponding S,S,S-tributylphosphorotrithioate are disclosed in U.S. Pat. Nos. 2,943,107; 3,885,002 and 5,189,195. In the process disclosed in U.S. Pat. No. 2,943,107, the oxidizing agent is selected from air, molecular oxygen, peroxide, persulfates and chlorine water. The oxidizing agent for the process of U.S. Pat. No. 3,885,002 is molecular oxygen itself or in the form of air. In the process described in U.S. Pat. No. 5,189,195, peroxide was used as the oxidizing agent.

The disadvantage of each of these known oxidizing agents is the need to treat the crude oxidation product to improve the purity of the S,S,S-tributylphosphorotrithioate. These known processes require at least two (and often three) phase separation treatments to obtain a high purity product. Multiple extractions result in lost product and decreased yield. Such purification treatments also increase production time and expense.

Perborates and percarbonates are known materials. Sodium perborate is a large scale industrial chemical which is used as a source of active oxygen in detergents, as an alternative to various forms of chlorine for fiber bleaching, and as a mild antiseptic and mouthwash. Sodium perborate has also been investigated as a possible oxidizing agent for the production of azo compounds from aniline as described in S. M. Mehta and M. V. Vakilwala, *J. Am. Chem. Soc.*, 74, 563 (1952) and L. Huestis, *J. Chem. Ed.*, 54, 327 (1977) and for alkenylboronic acids as described in D. S. Matteson and R. J. Moody, *J. Org. Chem.*, 45, 1091 (1980). To date, however, perborates and percarbonates have not been used to oxidize materials such as S,S,S-tributylphosphorotrithioite.

SUMMARY OF THE INVENTION

It is an object of the present invention to provide a process for the oxidation of S,S,S-tributylphosphorotrithioite which yields S,S,S-tributylphosphorotrithioate of high purity in high yields.

It is another object of the present invention to provide a simple, efficient process for the oxidation of S,S,S-tributylphosphorotrithioite to S,S,S-tributylphosphorotrithioate.

It is also an object of the present invention to provide a process for producing high quality S,S,S-tributylphosphorotrithioate in which high purity product may be recovered after a single phase separation.

It is a further object of the present invention to provide a process for oxidizing S,S,S-tributylphosphorotrithioite which may be carried out under sufficiently mild conditions that no special equipment is required.

These and other objects which will be apparent to those skilled in the art are accomplished by oxidizing S,S,S-tributylphosphorotrithioite with a perborate or percarbonate at a pH of from about 6 to about 12 and at a temperature of from about 40° to about 65° C. Alkali metal perborates are preferred with sodium perborate being the most preferred oxidizing agent.

DETAILED DESCRIPTION OF THE INVENTION

The S,S,S-tributylphosphorotrithioite (hereinafter referred to as "phosphite") used as the starting material in the process of the present invention may be made by any of the known processes. Such processes are disclosed, for example, in U.S. Pat. No. 2,943,107; U.S. Pat. No. 2,682,554; U.S. Pat. No. 3,885,002; and U.S. Pat. No. 5,183,916.

The phosphite may be used with or without a solvent in the process of the present invention. It is preferred, however, that it be used without a solvent. Where the phosphite is used in solution, any of the known organic solvents may generally be used. Toluene is an example of a suitable solvent.

The oxidizing agents useful in the practice of the process of the present invention are any of the known perborates and percarbonates. Examples of these known oxidizing agents include: sodium perborate monohydrate, sodium perborate tetrahydrate and sodium percarbonate. Perborates, particularly alkali metal perborates are preferred. Sodium perborate in its various hydrate forms is particularly preferred.

High concentrations of sodium percarbonate are not preferred because under some conditions, carbon dioxide gas (indicated by foaming) is generated. This carbon dioxide could cause problems when the oxidation reaction is carried out on a large production scale.

The oxidizing agent is generally used in a quantity such that at least one mole of oxidizing agent is present for every mole of phosphite. It is preferred that from about 1.0 to about 1.4 moles of oxidizing agent be present for every mole of phosphite to be oxidized.

The perborate or percarbonate is generally used in the form of a solid but it may also be used as a solution in, for example, acetic acid and water. It is preferred that the perborate or percarbonate be in the form of a coarse powder. The particle size of the powder is not an essential feature of the invention.

The oxidation is carried out at a pH of from about 6 to about 12, preferably from about 6 to about 7.

The reaction is conducted at a temperature of from about 40° to about 65° C., preferably from about 60° to about 65° C. When shorter reaction times are desired, the reaction temperature is preferably maintained at from about 60° to about 65° C.

The process of the present invention generally produces yields of about 99% of theoretical in reaction times of from about 2 to about 6 hours. Commercially available equipment may be used in the conduct of the process of the present invention. Due to the relatively mild reaction conditions employed in the process of the present invention, expensive equipment designed specifically for use in this process is not required.

The process of the present invention is particularly advantageous in that high purity S,S,S-tributylphosphorotrithioate may be easily recovered. The product may, for example, be recovered by simple phase separation of the aqueous and organic phases. Only one phase separation is necessary to recover high purity product in high yield. Although more than one phase separation may be performed to recover the product of the present invention, such multiple separations are not usually desirable because product yield is reduced after each separation.

Having thus described our invention, the following examples are given as being illustrative thereof. All parts and percentages given in these examples are parts by weight and percentages by weight, unless otherwise indicated.

EXAMPLES

Example 1

A 3000 ml 4-necked round-bottomed flask was equipped with an overhead stirrer, thermometer, pH probe and a 1000 ml addition funnel, a heating mantle and an ice bath. 892.5 grams (3.0 moles) of phosphite were charged to the flask and agitation of the flask was begun. The flask was heated to 60° C. and 15 grams of the total amount of perborate to be added (329.4 grams (3 moles+10% excess) of sodium perborate monohydrate) were added to the flask. Dilute hydrochloric acid was added dropwise at a rate of 3 drops per second. The exotherm of the reaction was allowed to increase the flask temperature to no greater than 65° C. The perborate was added in 15 gram increments every 3 minutes while dilute hydrochloric acid was being simultaneously added for a period of approximately 60 minutes. The addition of dilute hydrochloric acid was continued until a pH of 4 was reached. The contents of the flask were then heated for 30 minutes at 60° C. and analyzed for completeness of the reaction by gas chromatography. After the reaction had been completed (2–3 hours), the pH was adjusted to 10.5 with a 50% aqueous sodium hydroxide solution. The contents of the flask were then heated at 60° C. for 1 hour. 600 grams of water were then added to the flask and the flask contents were agitated for 15 minutes at 60° C. The aqueous and organic phases were separated. The aqueous phase contained less than 0.1% S,S,S-tributylphosphorotrithioate. The organic phase was steam stripped, dried and filtered. The yield of S,S,S-tributylphosphorotrithioate was 98.25% (Active Ingredient: 98.65%)

Example 2

A 500 ml 4-necked round-bottomed flask was equipped with a stirrer, thermometer, addition funnel and heating mantle. 148.7 grams (0.5 moles) phosphite and 184.7 grams (0.5 moles) sodium percarbonate trihydrate were added to the flask and heated to 60° C. with stirring. A 15% solution of hydrochloric acid was added over a 1 hour period while the temperature was maintained at 60° C. and the pH was kept at 4. 160 ml of 15% hydrochloric acid was added. The pH of the contents was subsequently determined to be 8.4. The yield of S,S,S-tributylphosphorotrithioate was 98%.

Example 3

The effect of reaction time and temperature was studied by repeating the procedure of Example 1 with the exception that the temperature and reaction times were varied. The results are reported in Table 1.

TABLE 1

| REACTION TEMP. | pH | REACTION TIME | % ACTIVE INGREDIENT |
|---|---|---|---|
| 40–45° C. | 6–7 | 6 hrs. | 99.0% |
| 50–55° C. | 6–7 | 4 hrs. | 98.7% |
| 60–65° C. | 6–7 | 2 hrs. | 98.8% |

Example 4

The effect of pH on the oxidation of the present invention was studied by repeating the procedure described in Example 1 with the exception that the pH of the reaction mixture was varied. The results of this study are reported in Table 2.

TABLE 2

| REACTION TEMP. | pH | REACTION TIME | % ACTIVE INGREDIENT | % YIELD |
|---|---|---|---|---|
| 60–65° C. | 6–7 | 2 hrs. | 98.8% | 99.1% |
| 60–65° C. | 8–9 | 3 hrs. | 98.8% | 99.0% |
| 60–65° C. | 11–12 | 4 hrs. | 98.2% | 98.4% |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of S,S,S-tributylphosphorotrithioate in which S,S,S-tributylphosphorotrithioite is oxidized with a perborate or a percarbonate at a temperature of from about 40° to about 65° C. and at a pH of from about 6 to about 12.

2. The process of claim 1 in which the oxidizing agent is a perborate.

3. The process of claim 1 in which the oxidizing agent is an alkali metal perborate.

4. The process of claim 1 in which the oxidizing agent is sodium perborate.

5. The process of claim 1 in which the oxidation is carried out at a pH of from about 6 to about 7.

6. The process of claim 1 in which the oxidation is carried out at a temperature of from about 60° to about 65° C.

7. The process of claim 1 in which the oxidizing agent is sodium percarbonate.

8. The process of claim 1 in which the S,S,S-tributylphosphorotrithioate is recovered from the reaction mixture by a single phase separation.

* * * * *